(12) United States Patent
Penhale et al.

(10) Patent No.: US 8,395,134 B2
(45) Date of Patent: Mar. 12, 2013

(54) RADIATION SOURCE CARTRIDGE AND MODULE CONTAINING SAME

(75) Inventors: Douglas Penhale, London (CA); Joseph Elku, Tillsonburg (CA); Bradley Hallett, London (CA)

(73) Assignee: Trojan Technologies (CA)

( * ) Notice: Subject to any disclaimer, the term of this patent is extended or adjusted under 35 U.S.C. 154(b) by 406 days.

(21) Appl. No.: 12/639,142

(22) Filed: Dec. 16, 2009

(65) Prior Publication Data

US 2010/0148094 A1 Jun. 17, 2010

Related U.S. Application Data

(60) Provisional application No. 61/193,686, filed on Dec. 16, 2008.

(51) Int. Cl.
*A61N 5/06* (2006.01)
*G01J 3/10* (2006.01)
*H05G 2/00* (2006.01)

(52) U.S. Cl. .................. 250/504 R; 250/493.1; 250/436; 250/431

(58) Field of Classification Search ............... 250/504 R, 250/493.1, 436, 431
See application file for complete search history.

(56) References Cited

U.S. PATENT DOCUMENTS

| 3,551,091 A | * | 12/1970 | Veloz ............................ 210/251 |
| 5,894,130 A | * | 4/1999 | Bach ............................ 250/436 |
| 2005/0000365 A1 | * | 1/2005 | Nelsen et al. .................. 96/224 |
| 2005/0247609 A1 | * | 11/2005 | Laing et al. ................... 210/109 |

OTHER PUBLICATIONS

Supplementary European Search Report.

* cited by examiner

*Primary Examiner* — Jack Berman
*Assistant Examiner* — Meenakshi Sahu
(74) *Attorney, Agent, or Firm* — Katten Muchin Rosenman LLP

(57) ABSTRACT

There is disclosed an elongate radiation source cartridge. The cartridge comprises: (i) an elongate radiation source assembly having a proximal portion and distal portion, the distal portion of the elongate radiation source assembly being unsupported, (ii) a housing coupled to the proximal portion of the elongate radiation source assembly, and (iii) a power supply disposed within the housing, the power supply in electrical communication with the elongate radiation source assembly (in certain embodiments the power supply is optional). The elongate radiation source assembly and the housing are in substantial alignment with respect to a longitudinal axis of the elongate radiation source cartridge.

39 Claims, 3 Drawing Sheets

RADIATION SOURCE CARTRIDGE AND MODULE CONTAINING SAME

CROSS-REFERENCE TO RELATED APPLICATION

The present application claims the benefit under 35 U.S.C. §119(e) of provisional patent application Ser. No. 61/193,686, filed Dec. 16, 2008, the contents of which are hereby incorporated by reference.

BACKGROUND OF THE INVENTION

1. Field of the Invention

In one of its aspects, the present invention relates to an elongate radiation source cartridge. In another of its aspects, the present invention relates to a radiation source module comprising the elongate radiation source cartridge.

2. Description of the Prior Art

Fluid treatment systems are known generally in the art.

For example, U.S. Pat. Nos. 4,482,809, 4,872,980 and 5,006,244 (all in the name of Maarschalkerweerd and all assigned to the assignee of the present invention and hereinafter referred to as the Maarschalkerweerd #1 Patents) all describe gravity fed fluid treatment systems which employ ultraviolet (UV) radiation.

Such systems include an array of UV lamp modules (e.g., frames) which include several UV lamps each of which are mounted within sleeves which extend between and are supported by a pair of legs which are attached to a cross-piece. The so-supported sleeves (containing the UV lamps) are immersed into a fluid to be treated which is then irradiated as required. The amount of radiation to which the fluid is exposed is determined by the proximity of the fluid to the lamps, the output wattage of the lamps and the flow rate of the fluid past the lamps. Typically, one or more UV sensors may be employed to monitor the UV output of the lamps and the fluid level is typically controlled, to some extent, downstream of the treatment device by means of level gates or the like.

The radiation source typically used in these systems is known as a low pressure ultraviolet radiation lamp. More recently, some of the systems have employed the so-called low pressure, high output (LPHO) ultraviolet radiation lamps and/or amalgam lamps. Both of these types of lamps are relatively long (48 inches or more).

U.S. Pat. Nos. 5,418,370, 5,539,210 and 5,590,390 (all in the name of Maarschalkerweerd and all assigned to the assignee of the present invention and hereinafter referred to as the Maarschalkerweerd #2 Patents) all describe an improved radiation source module for use in gravity fed fluid treatment systems which employ UV radiation. Generally, the improved radiation source module comprises a radiation source assembly (typically comprising a radiation source and a protective (e.g., quartz sleeve) sealingly cantilevered from a support member. The support member may further comprise appropriate means to secure the radiation source module in the gravity fed fluid treatment system.

U.S. Pat. No. 6,507,028 [Sarchese et al. (Sarchese)] teaches a radiation source module having a power supply that is adapted to be at least partially immersed in fluid being treated by the radiation source module.

United States patent publication 2007/0284315 [Collins et al. (Collins)] teaches a water disinfection apparatus in which elongate radiation sources are supported at both ends. One end of the water disinfection apparatus includes a power supply for the apparatus.

Notwithstanding the above advances in the art, there is still room for improvement.

Conventional radiation treatment systems feature a number of lamps that must be oriented in the fixed array (e.g., using one or more modules). In order to service the array, it is common that the array needs to be turned off and removed, compromising efficiency and/or disinfection. In addition, removal of the array normally requires a lifting device (e.g., a crane) due to the weight of the array. Conventional disinfection systems comprise a number of such arrays that are secured with respect to an effluent channel (e.g., an open channel comprising a flow of fluid). In this way, it is possible to increase the capacity of the system in a step-wise manner by increasing the number of lamps in the array or arrays in the channel.

Conventional fluid treatment systems also employ relatively low power density lamps of long length to reduce the overall number of lamps required in the fluid treatment system—see, for example, the Maarschalkerweerd #1 Patents. The use of such long lamps necessitated that they be fixed at both ends to reduce the effluent flow-induced stresses to acceptable levels.

Conventional radiation source modules contain multiple lamps that are coupled to the frame, optionally including a power supply for the radiation sources in the module. Thus, when it is desired to service a single lamp in the module, it is necessary to remove the entire module from service, replace (or otherwise service) the radiation source of interest and return the module to service. This necessitates that there be redundancy in the fluid treatment system so that acceptable levels of disinfection can be attained even when one or more radiation source modules are removed from the fluid flow for servicing.

In addition, servicing of conventional radiation source modules requires that qualified personnel in the field be available to carefully remove the radiation source module from service and to disconnect the appropriate electrical connections and reconnect them after the module has been serviced. In many cases, when more than a single lamp in a given module is being serviced, there is likelihood that incorrect electrical connections will be made thereby potentially compromising the operability of the module.

Accordingly, it would be desirable to have a radiation source cartridge which contains the radiation source and electrical components needed to operate the radiation source so that servicing thereof is facilitated. It would also be desirable if such a radiation source cartridge was capable of being coupled to the fluid treatment system in a unique manner so that there was a unique orientation of the radiation source with respect to other radiation sources in the fluid treatment system.

SUMMARY OF THE INVENTION

It is an object of the present invention to obviate or mitigate at least one of the above-mentioned disadvantages of the prior art.

It is another object of the present invention to provide a novel elongate radiation source cartridge.

Accordingly, in one of its aspects, the present invention provides an elongate radiation source cartridge comprising: (i) an elongate radiation source assembly having a proximal portion and distal portion, the distal portion of the elongate radiation source assembly being unsupported, (ii) a housing coupled to the proximal portion of the elongate radiation source assembly, and (iii) a power supply disposed within the housing, the power supply in electrical communication with the elongate radiation source assembly;

wherein the elongate radiation source assembly and the housing are in substantial alignment with respect to a longitudinal axis of the elongate radiation source cartridge.

In another of its aspects, the present invention provides an elongate radiation source cartridge comprising: (i) an elongate radiation source assembly having a proximal portion and distal portion, the distal portion of the elongate radiation source assembly being unsupported, (ii) a housing coupled to the proximal portion of the elongate radiation source assembly, the housing configured to allow only a single correct placement thereof in a cartridge holder of a radiation source module configured to be receive the housing;

wherein the elongate radiation source assembly and the housing are in substantial alignment with respect to a longitudinal axis of the elongate radiation source cartridge.

Accordingly, the present inventors have discovered a radiation source cartridge that, in a preferred embodiment, may be considered to be a discrete unit consisting of one lamp, one control circuit and one ballast (or other power supply) for the lamp. By using a shorter, relatively high power density radiation lamp, it is not necessary to secure the radiation source assembly at both ends and thus, the present radiation source cartridge may be considered to comprise a cantilevered radiation source. Preferably, one or more of the radiation source cartridges can be mounted substantially vertically into a holder that is fixed with respect to an effluent channel (e.g., an open channel containing a flow of fluid)—alternatively, the radiation source cartridges may be mounted in any configuration that results in the longitudinal axis of the elongate radiation sources being transverse (i.e., non-parallel) with respect to the direction of fluid flow through the effluent channel. In a preferred embodiment, by coupling the power supply (e.g., ballast) and radiation source relatively closely together, the distance between these two key elements is minimized thereby simplifying the electrical connections. Further, in these preferred embodiments, by having a power supply (e.g., ballast) mounted independently for each of the radiation sources, heat dissipation from the ballasts is greatly facilitated compared to known radiation source modules where the power supplies (e.g., ballasts) are mounted to the side of a channel in a cabinet or where a number of ballasts are included in a multiple lamp radiation source module. Servicing of the present radiation source cartridge is greatly facilitated in that a relatively light-weight cartridge comprising, primarily, a radiation source and a power supply (e.g., ballast) can be readily removed and replaced without disturbing other radiation source cartridges that are being employed in the fluid treatment system. The light-weight feature of the present radiation source cartridge allows for a service person to easily remove it without the need for lifting assistance. Removal of a single radiation source from a fluid treatment system has minimal impact on the disinfection performance of that system while the cartridge is being serviced.

BRIEF DESCRIPTION OF THE DRAWINGS

Embodiments of the present invention will be described with reference to the accompanying drawings, wherein like reference numerals denote like parts, and in which.

DETAILED DESCRIPTION OF THE PREFERRED EMBODIMENTS

Figure 1:
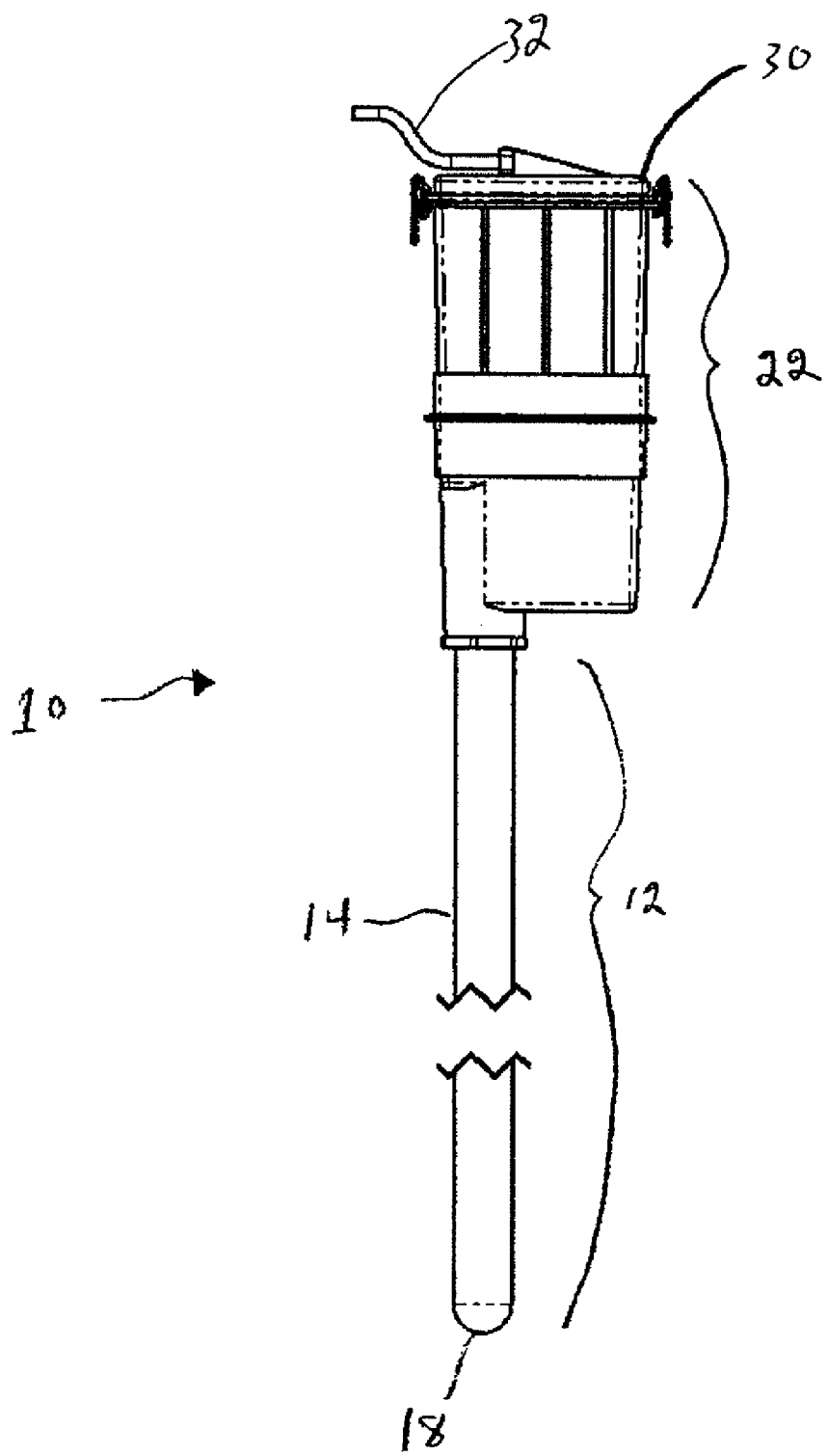
FIG. 1 illustrates a side elevation of a preferred embodiment of the present radiation source cartridge.

In one of its aspects, the present invention relates to a radiation source cartridge. Preferred embodiments of the radiation source cartridge may include any one or a combination of any two or more of any of the following features:
- the elongate radiation source assembly comprises an elongate radiation source disposed in an elongate protective sleeve;
- the radiation source has a radiation source length that is less than a protective sleeve length of the protective sleeve;
- the protective sleeve comprises an open proximal end that is coupled to the housing;
- the protective sleeve comprises a closed distal end that is unsupported;
- a proximal portion of the radiation source defines a fluid flow level limit;
- the fluid flow limit is spaced from a distal portion of the housing;
- the housing is elongate;
- a longitudinal axis of the housing is in substantial alignment with the longitudinal axis of the elongate radiation source cartridge;
- the elongate radiation source assembly and the housing are in a non-coaxial relationship;
- the elongate radiation source assembly and the housing are in a substantially coaxial relationship;
- the elongate radiation source assembly and the housing are coupled in a substantially fluid tight manner;
- the power supply comprises a ballast;
- the housing comprises a first cross-section taken along a plane normal to the longitudinal axis, the first cross-section having a shape that is symmetrical with respect to no more than a single axis taken through a mid-point of the shape;
- the shape is rectilinear;
- the shape is triangular;
- the shape is curvilinear.
- the shape is elongate with a pair of opposed non-symmetrical end portions;
- one end portion is linear and the other end portion is curved;
- the housing comprises a second cross-section taken along a plane parallel to the longitudinal axis, the second cross-section having a shape that tapers with respect to the longitudinal axis;
- the elongate radiation source assembly has a longitudinal length of less than about 48 inches;
- the elongate radiation source assembly has a longitudinal length in the range of from about 12 inches to about 42 inches;
- the elongate radiation source assembly has a longitudinal length in the range of from about 24 inches to about 42 inches;
- the elongate radiation source assembly has a longitudinal length in the range of from about 30 inches to about 42 inches;
- the elongate radiation source assembly has a longitudinal length in the range of from about 32 inches to about 36 inches;
- it comprises only a single elongate radiation source assembly;

the elongate radiation source assembly comprises an ultraviolet radiation source;

the elongate radiation source assembly comprises a medium pressure ultraviolet radiation source;

the elongate radiation source assembly comprises a low pressure, high output (LPHO) ultraviolet radiation source; and/or the elongate radiation source assembly comprises a dielectric barrier discharge (DBD) radiation source.

In another of its aspects, the present invention relates to a radiation source module. Preferred embodiments of the radiation source module may include any one or a combination of any two or more of any of the following features:

it further comprises a mounting plate for securing the plurality of elongate radiation source cartridges;

the mounting plate comprises an aperture for each elongate radiation source cartridge;

the aperture is coupled at its periphery to a cartridge holder element;

the cartridge holder and the housing have a substantially complementary cross-sectional shape;

the substantially complementary shape is configured to allow only a single correct placement of the housing in the cartridge holder;

the mounting plate comprises at least one mounting element for mounting the radiation source module in a fluid treatment system;

the mounting plate comprises a pair of mounting elements for mounting the radiation source module in a fluid treatment system; and/or the mounting plate comprises a pair of opposed mounting elements for mounting the radiation source module in a fluid treatment system.

Figure 2:
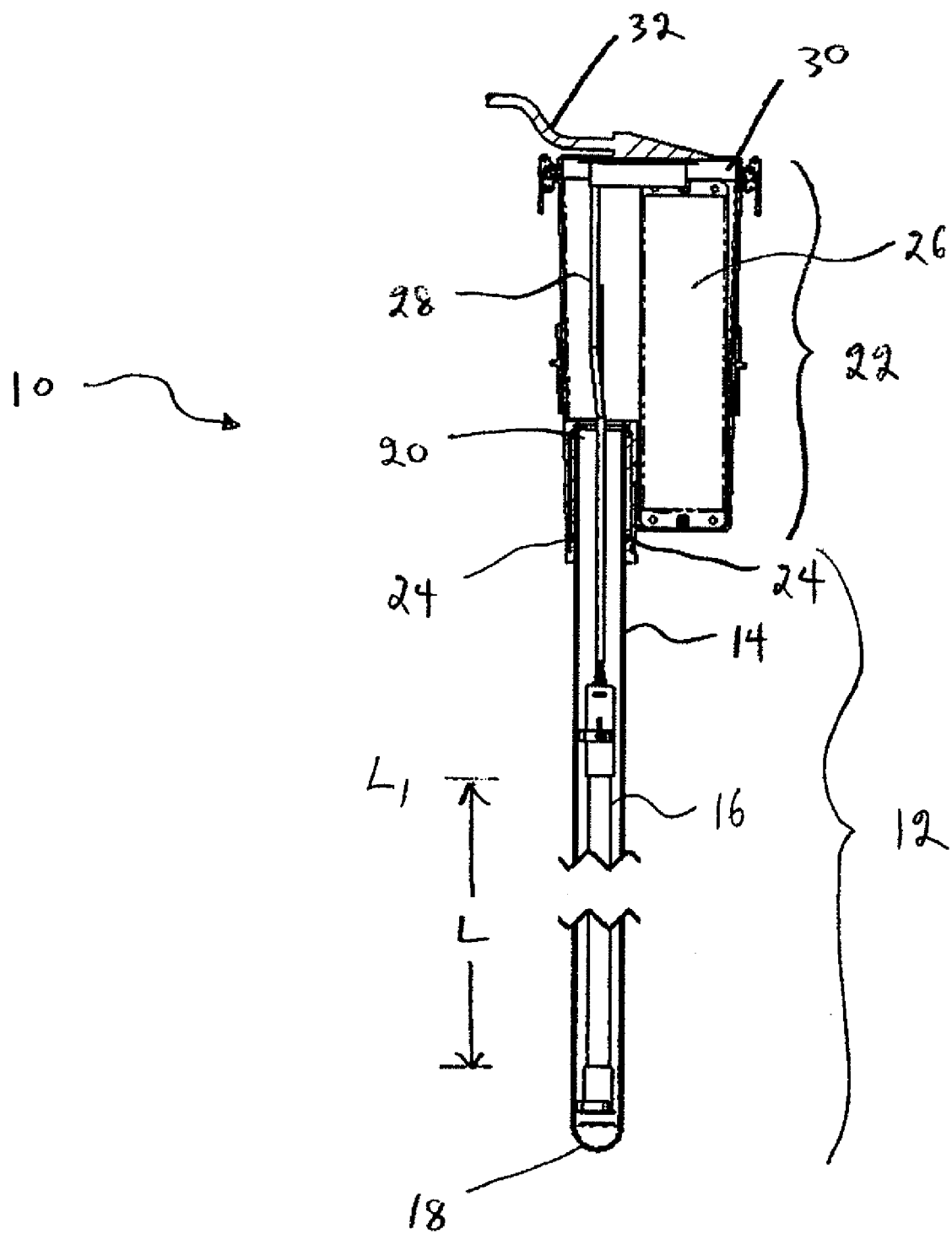
FIG. 2 illustrates a cross-sectional view of the radiation source cartridge illustrated in FIG. 1.

With reference to FIGS. 1 and 2, there is illustrated a radiation source cartridge 10. Radiation source cartridge 10 comprises a radiation source assembly 12.

Radiation source assembly 12 comprises a protective sleeve 14 in which is disposed a radiation source 16. Radiation source 16 has an arc-length, L, which corresponds to the length of radiation source 16 that emits radiation. As illustrated in FIG. 2, arc-length L is shorter than the length of protective sleeve 14 of radiation source assembly 12.

Protective sleeve 14 can be made of any radiation transparent material—e.g., quartz or the like. Protective sleeve 14 comprises a closed end 18 and an open end 20.

Protective sleeve 14 is coupled to an elongate housing 22. Preferably, this coupling is achieved in a fluid tight manner through the use of one or more seals 24 or the like. Disposed in housing 22 is power supply 26 for radiation source 16. Preferably, the power supply is a ballast or the like. An electrical connection between radiation source 16 and power supply 26 is made by an electrical connector 28.

Housing 22 further comprises a lid 30 having incorporated therein an electrical connector 32 which is also an electrical communication with power supply 26.

As can be seen from FIGS. 1 and 2, radiation source assembly 12 is cantilevered inasmuch as closed end 18 of protective sleeve 14 is unsupported.

As is also evident from FIG. 2, arc-length L is shorter than the distance between housing 22 and closed end 18 of protective sleeve 14 to define a fluid flow limit L1 that is spaced from the distal portion of housing 22.

Preferably, housing 22 is itself elongate and has a longitudinal axis that is in alignment (co-axially or non-coaxially) with the longitudinal axis elongate radiation source cartridge 10.

In a preferred embodiment of the present radiation source cartridge, housing 22 is configured to have a shape that will allow for unique placement in an array of other radiation source cartridges. Thus, it is preferred that the housing has a cross section taken along a plane normal to the longitudinal axis of the radiation source cartridge such that the shape of this cross section is symmetrical with respect to not more than a single axis taken through a mid-point of the shape—i.e., the shape of the cross-section has no axis of symmetry or only one axis of symmetry. In one preferred embodiment, the shape is rectilinear. In another embodiment, the shape is triangular. In yet another embodiment, the shape is curvilinear.

In another preferred embodiment, it is preferred that the housing have a cross sectional shape taken along a plane parallel to the longitudinal axis of the radiation source cartridge that tapers with respect to the longitudinal axis. Preferably, the direction of the taper is such that there is a narrowing in a direction toward closed end 18 of protective sleeve 14. As will be discussed below, this allows for secure placement of the radiation source cartridge in a radiation source module.

Preferably, radiation source 16 is a ultraviolet radiation source. Typically, this will be in the form of an ultraviolet radiation lamp. In one embodiment, the radiation source is a medium pressure ultraviolet radiation lamp. In another embodiment, the radiation source is a low pressure, high output (LPHO) ultraviolet radiation source. In another embodiment, the radiation source is a dielectric barrier discharge (DBD) radiation source.

Preferably, the length of radiation source assembly 12 is less than about 48 inches, more preferably in the range of from about 12 inches to about 42 inches, more preferably in the range of from about 24 inches to about 42 inches, more preferably in the range of from about 30 inches to about 42 inches, more preferably in the range of from about 32 inches to about 38 inches.

Ideally, radiation source cartridge 10 includes a single radiation source assembly and a single power supply (e.g., ballast). This discrete unit then becomes replaceable as will be described below.

Figure 3:
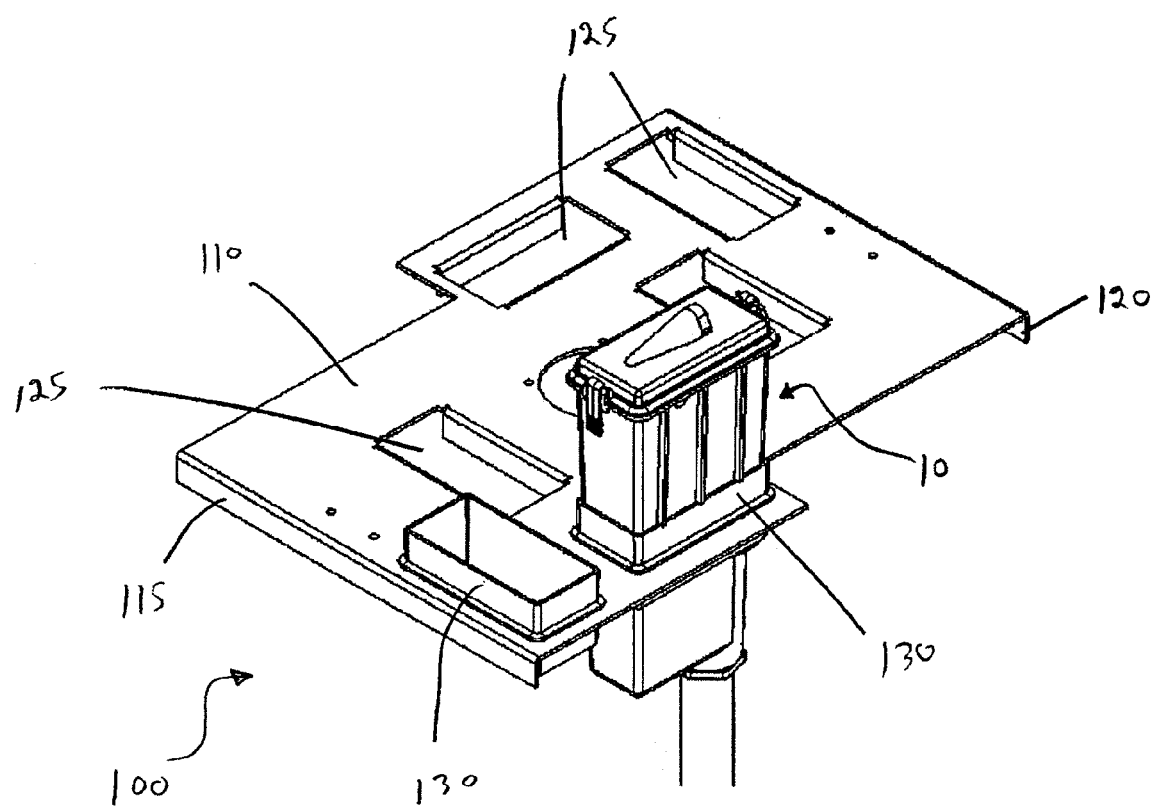
FIG. 3 illustrates placement of the radiation source cartridge illustrated in FIGS. 1 and 2 in a mounting plate for use in a fluid treatment system.

With reference to FIG. 3, there is illustrated a portion of a radiation source module 100. Radiation source module 100 comprises a mounting plate 110 having a pair of opposed rails 115,120.

Mounting plate 110 comprises a series of apertures 125. The cartridge holder 130 is coupled to the periphery of each aperture 125 (for clarity, not all of apertures 125 illustrated in FIG. 3 have a cartridge holder associated with them).

As shown in FIG. 3, radiation source cartridge 10 is placed in aperture 125 such that a friction fit is made with cartridge holder 130. By selecting housing 22 to have a cross-sectional shape that is substantially complementary with the cross-sectional shape of cartridge holder 130, radiation source cartridge 10 can be only placed in two configurations in mounting plate 110. This ensures substantially correct placement of radiation source cartridge 10 every time. Of course it is possible to modify the cross-sectional shape of cartridge holder 130 to have no more than a single axis of symmetry through its mid-point—the result would be that each radiation source cartridge 10 could be placed in only one configuration in mounting plate 110 thereby improving the precision by which the radiation source assemblies are oriented in a given array. A number of radiation source cartridges 10 are then placed in each of apertures 125 and mounting plate 110 in a similar manner. The result is a radiation source module having a plurality of radiation source cartridges 10 that are secured in a prescribed array. Radiation source module 100 can then be put in a fluid treatment system—for example, by supporting mounting rails 115,120 on the sides of an open channel having a flow of fluid therein. In such a configuration, radiation source assembly 12 is cantilevered and closed end 18 of protective sleeve 14 is disposed above the floor of the open channel (not shown).

It is possible to use multiple radiation source modules disposed serially in the fluid treatment system. For example, mounting rails 115,120 could be supported by cross-supports (not shown) that span the width of the open channel. Preferably, one or more baffles are placed between serially adjacent radiation source modules—for example using the arrangement described in copending U.S. patent application Ser. No. 11/840,590 (Traubenberg et al.), filed on Aug. 17, 2008. Using such a baffle arrangement, it is possible to design the system such that the fluid level rises above L1 mentioned above and reaches the surface of housing 22—this allows for cooling of the power supply (e.g., ballast) disposed in housing 22. The risk of short circuiting (i.e., fluid not being sufficiently treated) is obviated for the reasons described in Traubenberg et al.

While it is preferred to mount radiation source cartridges 10 in a substantially vertical orientation in the fluid treatment system, radiation source cartridges 10 also may be mounted in any configuration that results in the longitudinal axis of the elongate radiation sources being transverse (i.e., non-parallel) with respect to the direction of fluid flow through the effluent channel.

When it is desired to replace a radiation source, it is a relatively simple matter to disconnect the electrical connection made with connector 32, remove the entire cartridge 10, insert a new cartridge 10 and reconnect the electricity to connector 32. This can be done without removing mounting plate 110 from service or disturbing operation of other radiation source cartridges 10 that are secured to mounting plate 110.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. An elongate radiation source cartridge comprising: (i) an elongate radiation source assembly having a proximal portion and distal portion, the distal portion of the elongate radiation source assembly being unsupported, (ii) a housing coupled to the proximal portion of the elongate radiation source assembly, and (iii) a power supply disposed within the housing, the power supply in electrical communication with the elongate radiation source assembly;
wherein: (i) the elongate radiation source assembly and the housing are in substantial alignment with respect to a longitudinal axis of the elongate radiation source cartridge, and (ii) the elongate radiation source assembly comprises an elongate radiation source having an arc length that is longitudinally spaced from a distal end of the housing.

2. The elongate radiation source cartridge defined in claim 1, wherein the elongate radiation source assembly comprises an elongate radiation source disposed in an elongate protective sleeve.

3. The elongate radiation source cartridge defined in claim 2, wherein the radiation source has a radiation source length that is less than a protective sleeve length of the protective sleeve.

4. The elongate radiation source cartridge defined in claim 2, wherein the protective sleeve comprises an open proximal end that is coupled to the housing.

5. The elongate radiation source cartridge defined in claim 2, wherein the protective sleeve comprises a closed distal end that is unsupported.

6. The elongate radiation source cartridge defined in claim 1, wherein a proximal portion of the radiation source defines a fluid flow level limit.

7. The elongate radiation source cartridge defined in claim 6, wherein the fluid flow limit is spaced from a distal portion of the housing.

8. The elongate radiation source cartridge defined in claim 1, wherein the housing is elongate.

9. The elongate radiation source cartridge defined in claim 8, wherein a longitudinal axis of the housing is in substantial alignment with the longitudinal axis of the elongate radiation source cartridge.

10. The elongate radiation source cartridge defined in claim 8, wherein the elongate radiation source assembly and the housing are in a non-coaxial relationship.

11. The elongate radiation source cartridge defined in claim 8, wherein the elongate radiation source assembly and the housing are in a substantially coaxial relationship.

12. The elongate radiation source cartridge defined in claim 1, wherein the housing comprises a first cross-section taken along a plane normal to the longitudinal axis, the first cross-section having a shape that is symmetrical with respect to no more than a single axis taken through a mid-point of the shape.

13. The elongate radiation source cartridge defined in claim 12, wherein the shape is rectilinear.

14. The elongate radiation source cartridge defined in claim 12, wherein the shape is triangular.

15. The elongate radiation source cartridge defined in claim 12, wherein the shape is curvilinear.

16. The elongate radiation source cartridge defined in claim 12, wherein the shape is elongate with a pair of opposed non-symmetrical end portions.

17. The elongate radiation source cartridge defined in claim 16, wherein one end portion is linear and the other end portion is curved.

18. The elongate radiation source cartridge defined in claim 1, wherein the housing comprises a second cross-section taken along a plane parallel to the longitudinal axis, the second cross-section having a shape that tapers with respect to the longitudinal axis.

19. The elongate radiation source cartridge defined in claim 1, wherein the elongate radiation source assembly has a longitudinal length in the range of from about 30 inches to about 42 inches.

20. The elongate radiation source cartridge defined in claim 1, wherein the elongate radiation source assembly has a longitudinal length in the range of from about 32 inches to about 36 inches.

21. The elongate radiation source cartridge defined in claim 1, wherein the elongate radiation source assembly comprises an ultraviolet radiation source.

22. A radiation source module comprising a plurality of the elongate radiation source cartridges defined in claim 1.

23. The radiation source module defined in claim 22, further comprising a mounting plate for securing the plurality of elongate radiation source cartridges.

24. The radiation source module defined in claim 23, wherein the mounting plate comprises an aperture for each elongate radiation source cartridge.

25. The radiation source module defined in claim 24, wherein the aperature is coupled at its periphery to a cartridge holder element.

26. The radiation source module defined in claim 25, wherein the cartridge holder and the housing have a substantially complementary cross-sectional shape.

27. The radiation source module defined in claim 26, wherein the substantially complementary shape is configured to allow only a single correct placement of the housing in the cartridge holder.

28. The radiation source module defined in claim 22, wherein the mounting plate comprises at least one mounting element for mounting the radiation source module in a fluid treatment system.

29. The radiation source module defined in claim 22, wherein the mounting plate comprises a pair of mounting elements for mounting the radiation source module in a fluid treatment system.

30. The radiation source module defined in claim 22, wherein the mounting plate comprises a pair of opposed mounting elements for mounting the radiation source module in a fluid treatment system.

31. An elongate radiation source cartridge comprising: (i) an elongate radiation source assembly having a proximal portion and distal portion, the distal portion of the elongate radiation source assembly being unsupported, (ii) a housing coupled to the proximal portion of the elongate radiation source assembly, the housing configured to allow only a single correct placement thereof in a cartridge holder of a radiation source module configured to be receive the housing; wherein: (i) the elongate radiation source assembly and the housing are in substantial alignment with respect to a longitudinal axis of the elongate radiation source cartridge; and (ii) the elongate radiation source assembly comprises an elongate radiation source configured to have an arc length that is longitudinally spaced from a distal end of the housing.

32. The elongate radiation source cartridge defined in claim 31, further comprising:
(iii) a power supply disposed within the housing, the power supply in electrical communication with the elongate radiation source assembly.

33. The elongate radiation source cartridge defined in claim 31, wherein the housing comprises a first cross-section taken along a plane normal to the longitudinal axis, the first cross-section having a shape that is symmetrical with respect to no more than a single axis taken through a mid-point of the shape.

34. The elongate radiation source cartridge defined in claim 33, wherein the shape is rectilinear.

35. The elongate radiation source cartridge defined in claim 33, wherein the shape is triangular.

36. The elongate radiation source cartridge defined in claim 33, wherein the shape is curvilinear.

37. The elongate radiation source cartridge defined in claim 33, wherein the shape is elongate with a pair of opposed non-symmetrical end portions.

38. The elongate radiation source cartridge defined in claim 37, wherein one end portion is linear and the other end portion is curved.

39. The elongate radiation source cartridge defined in claim 31, wherein the housing comprises a second cross-section taken along a plane parallel to the longitudinal axis, the second cross-section having a shape that tapers with respect to the longitudinal axis.

* * * * *